US012334216B2

(12) United States Patent
Wong et al.

(10) Patent No.: US 12,334,216 B2
(45) Date of Patent: Jun. 17, 2025

(54) AUTOMATIC AND REMOTE VISUO-MECHANICS AUDITING

(71) Applicant: KYNDRYL, INC.

(72) Inventors: Eric Wong, Caulfield South (AU); Jorge Andres Moros Ortiz, Canberra (AU); Bahman Tahayori, Altona North (AU); Mahtab Mirmomeni, Vermont South (AU); Rahil Garnavi, Macleod (AU)

(73) Assignee: Kyndryl, Inc., New York, NY (US)

( * ) Notice: Subject to any disclaimer, the term of this patent is extended or adjusted under 35 U.S.C. 154(b) by 487 days.

(21) Appl. No.: 17/393,816

(22) Filed: Aug. 4, 2021

(65) Prior Publication Data

US 2023/0043368 A1    Feb. 9, 2023

(51) Int. Cl.
| | |
|---|---|
| G16H 40/67 | (2018.01) |
| A61B 3/00 | (2006.01) |
| G05B 19/042 | (2006.01) |
| G16H 10/60 | (2018.01) |
| G16H 50/30 | (2018.01) |
| G16H 50/70 | (2018.01) |
| G16H 70/20 | (2018.01) |

(52) U.S. Cl.
CPC ........... *G16H 40/67* (2018.01); *A61B 3/0025* (2013.01); *G05B 19/042* (2013.01); *G16H 10/60* (2018.01); *G16H 50/30* (2018.01); *G16H 50/70* (2018.01); *G16H 70/20* (2018.01); *G05B 2219/24084* (2013.01)

(58) Field of Classification Search
CPC ........ G16H 40/67; G16H 10/60; G16H 50/30; G16H 50/70; G16H 70/20; A61B 3/0025; A61B 3/00; G05B 19/042; G05B 2219/24084
See application file for complete search history.

(56) References Cited

U.S. PATENT DOCUMENTS

| | | | |
|---|---|---|---|
| 8,684,922 B2 | 4/2014 | Tran | |
| 9,202,443 B2 | 12/2015 | Perez | |
| 11,582,338 B2* | 2/2023 | Grajales | ................. G16H 20/00 |
| 2009/0018407 A1* | 1/2009 | Jung | ...................... A61B 3/113 705/2 |
| 2017/0042421 A1* | 2/2017 | Wallace | ................. A61B 3/107 |
| 2018/0153399 A1* | 6/2018 | Fink | ......................... A61B 3/14 |
| 2018/0220984 A1 | 8/2018 | Brauner | |
| 2018/0274974 A1 | 9/2018 | Wang | |

(Continued)

FOREIGN PATENT DOCUMENTS

| | | |
|---|---|---|
| CN | 101363580 A | 2/2009 |
| JP | 2019517850 A | 6/2019 |

OTHER PUBLICATIONS

For Eyes, Should You Rest Your Eyes Before an Eye Exam?, Feb. 25, 2020 (Year: 2020).*

*Primary Examiner* — Shahid Merchant
*Assistant Examiner* — David Choi
(74) *Attorney, Agent, or Firm* — Erik Swanson; Andrew D. Wright; Calderon, Safran & Wright, P.C.

(57) ABSTRACT

An eye test administered to a remote subject over a computer network, where sensors provide feedback through the computer network so that light source position, light source brightness and/or a display configuration and/or parameter setting related to a visual display that is used to implement the remote eye test.

10 Claims, 3 Drawing Sheets

(56) References Cited

U.S. PATENT DOCUMENTS

| | | |
|---|---|---|
| 2019/0239790 A1* | 8/2019 | Gross ................... G16H 50/70 |
| 2019/0290118 A1* | 9/2019 | Jha ..................... A61B 3/0008 |
| 2019/0336046 A1 | 11/2019 | Shuster |
| 2020/0138285 A1 | 5/2020 | Antony |
| 2020/0229770 A1 | 7/2020 | Sedai |
| 2020/0364539 A1 | 11/2020 | Anisimov |
| 2022/0354440 A1* | 11/2022 | Grajales ................ G16H 50/30 |
| 2023/0255473 A1* | 8/2023 | Srinivasan ............ A61B 3/028 |
| | | 351/222 |

* cited by examiner

AUTOMATIC AND REMOTE VISUO-MECHANICS AUDITING

BACKGROUND

The present invention relates generally to the field of visuo-mechanics and more particularly to visuo-mechanics auditing. As the term is used in this document, "visuo-mechanics" includes a broad scope of parameters including: the positioning, the distance, the movement, the sound and the touch sense (this touch sense portion of visuo-mechanics is sometimes referred to as visuo-haptics).

SUMMARY

According to an aspect of the present invention, there is a method, computer program product and/or system that performs the following operations (not necessarily in the following order): (i) opening a data communication session between an end user computer system of a first user and a remote eye test server computer over a communication network; (ii) during the data communication session, administering, by the eye test server computer, an automated eye test that tests a set of characteristic(s) relating to vision of the first user; (iii) during the administration of the eye test, sending, by the eye test server computer, over the communication network and to the end user computer system, an instruction to make an environmental adjustment, with the environmental adjust including an adjustment a location of a first lamp included in an environment in which the first user computer system and the first user are located; and (iv) receiving, by the eye test server computer, over the communication network and from the computer device, a first confirmation communication indicating that the environmental adjustment has been made.

DETAILED DESCRIPTION

Figure 1:
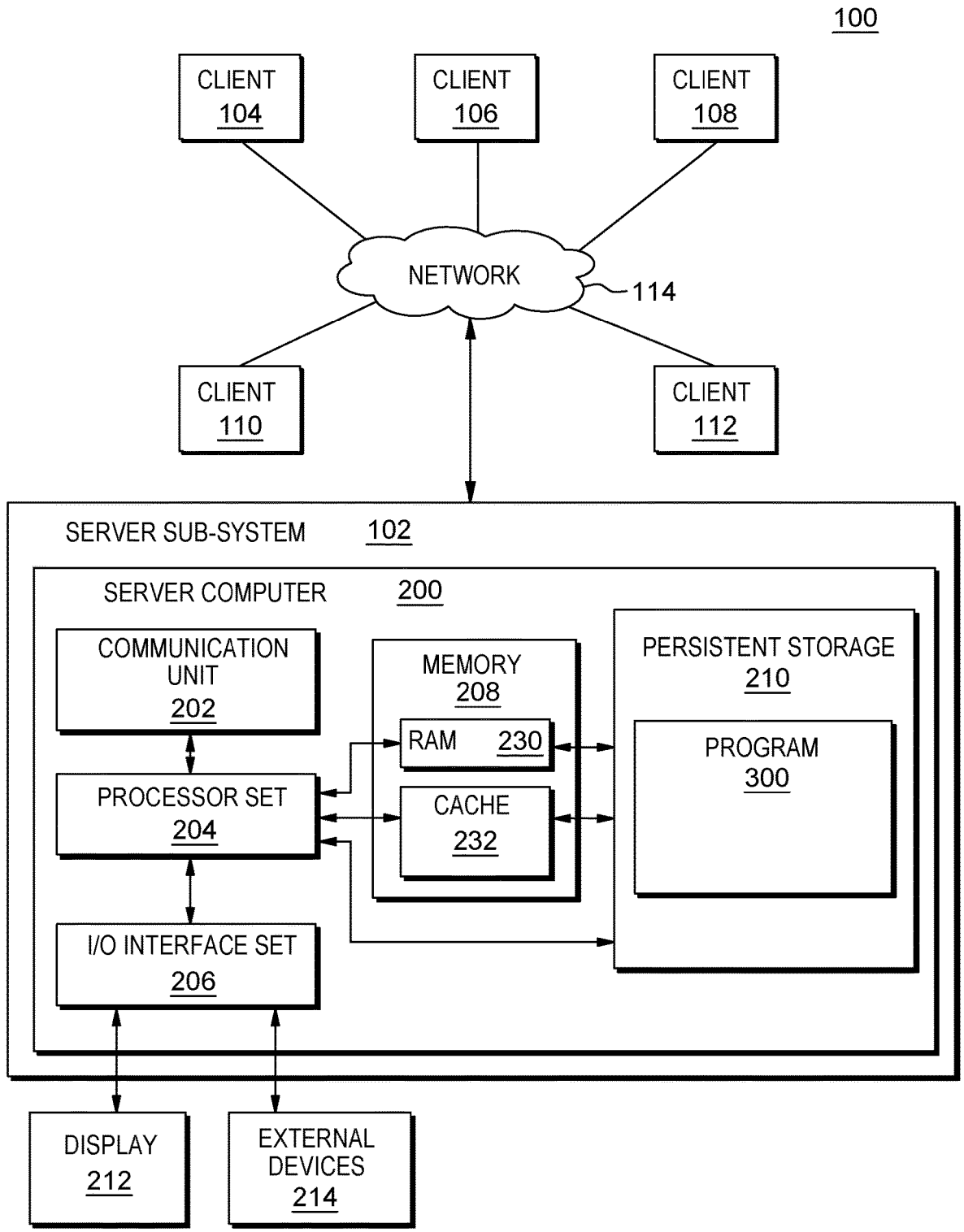
FIG. 1 is a block diagram view of a first embodiment of a system according to the present invention.

This Detailed Description section is divided into the following subsections: (i) The Hardware and Software Environment; (ii) Example Embodiment; (iii) Further Comments and/or Embodiments; and (iv) Definitions.

I. The Hardware and Software Environment

The present invention may be a system, a method, and/or a computer program product at any possible technical detail level of integration. The computer program product may include a computer readable storage medium (or media) having computer readable program instructions thereon for causing a processor to carry out aspects of the present invention. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (for example, light pulses passing through a fiber-optic cable), or electrical signals transmitted through a wire.

A "storage device" is hereby defined to be anything made or adapted to store computer code in a manner so that the computer code can be accessed by a computer processor. A storage device typically includes a storage medium, which is the material in, or on, which the data of the computer code is stored. A single "storage device" may have: (i) multiple discrete portions that are spaced apart, or distributed (for example, a set of six solid state storage devices respectively located in six laptop computers that collectively store a single computer program); and/or (ii) may use multiple storage media (for example, a set of computer code that is partially stored in as magnetic domains in a computer's non-volatile storage and partially stored in a set of semiconductor switches in the computer's volatile memory). The term "storage medium" should be construed to cover situations where multiple different types of storage media are used.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As shown in FIG. 1, networked computers system 100 is an embodiment of a hardware and software environment for use with various embodiments of the present invention. Networked computers system 100 includes: server subsystem 102 (sometimes herein referred to, more simply, as subsystem 102); client subsystems 104, 106, 108, 110, 112; and communication network 114. Server subsystem 102 includes: server computer 200; communication unit 202; processor set 204; input/output (I/O) interface set 206; memory 208; persistent storage 210; display 212; external device(s) 214; random access memory (RAM) 230; cache 232; and program 300.

Subsystem 102 may be a laptop computer, tablet computer, netbook computer, personal computer (PC), a desktop computer, a personal digital assistant (PDA), a smart phone, or any other type of computer (see definition of "computer" in Definitions section, below). Program 300 is a collection of machine readable instructions and/or data that is used to create, manage and control certain software functions that will be discussed in detail, below, in the Example Embodiment subsection of this Detailed Description section.

Subsystem 102 is capable of communicating with other computer subsystems via communication network 114. Network 114 can be, for example, a local area network (LAN), a wide area network (WAN) such as the Internet, or a combination of the two, and can include wired, wireless, or fiber optic connections. In general, network 114 can be any combination of connections and protocols that will support communications between server and client subsystems.

Subsystem 102 is shown as a block diagram with many double arrows. These double arrows (no separate reference numerals) represent a communications fabric, which provides communications between various components of subsystem 102. This communications fabric can be implemented with any architecture designed for passing data and/or control information between processors (such as microprocessors, communications and network processors, etc.), system memory, peripheral devices, and any other hardware components within a computer system. For example, the communications fabric can be implemented, at least in part, with one or more buses.

Memory 208 and persistent storage 210 are computer-readable storage media. In general, memory 208 can include any suitable volatile or non-volatile computer-readable storage media. It is further noted that, now and/or in the near future: (i) external device(s) 214 may be able to supply, some or all, memory for subsystem 102; and/or (ii) devices external to subsystem 102 may be able to provide memory for subsystem 102. Both memory 208 and persistent storage 210: (i) store data in a manner that is less transient than a signal in transit; and (ii) store data on a tangible medium (such as magnetic or optical domains). In this embodiment, memory 208 is volatile storage, while persistent storage 210 provides nonvolatile storage. The media used by persistent storage 210 may also be removable. For example, a removable hard drive may be used for persistent storage 210. Other examples include optical and magnetic disks, thumb drives, and smart cards that are inserted into a drive for transfer onto another computer-readable storage medium that is also part of persistent storage 210.

Communications unit 202 provides for communications with other data processing systems or devices external to subsystem 102. In these examples, communications unit 202 includes one or more network interface cards. Communications unit 202 may provide communications through the use of either or both physical and wireless communications links. Any software modules discussed herein may be downloaded to a persistent storage device (such as persistent storage 210) through a communications unit (such as communications unit 202).

I/O interface set 206 allows for input and output of data with other devices that may be connected locally in data communication with server computer 200. For example, I/O interface set 206 provides a connection to external device set 214. External device set 214 will typically include devices such as a keyboard, keypad, a touch screen, and/or some other suitable input device. External device set 214 can also include portable computer-readable storage media such as, for example, thumb drives, portable optical or magnetic disks, and memory cards. Software and data used to practice embodiments of the present invention, for example, program 300, can be stored on such portable computer-readable storage media. I/O interface set 206 also connects in data communication with display 212. Display 212 is a display device that provides a mechanism to display data to a user and may be, for example, a computer monitor or a smart phone display screen.

In this embodiment, program 300 is stored in persistent storage 210 for access and/or execution by one or more computer processors of processor set 204, usually through one or more memories of memory 208. It will be understood by those of skill in the art that program 300 may be stored in a more highly distributed manner during its run time and/or when it is not running. Program 300 may include both machine readable and performable instructions and/or substantive data (that is, the type of data stored in a database). In this particular embodiment, persistent storage 210 includes a magnetic hard disk drive. To name some possible variations, persistent storage 210 may include a solid state hard drive, a semiconductor storage device, read-only memory (ROM), erasable programmable read-only memory (EPROM), flash memory, or any other computer-readable storage media that is capable of storing program instructions or digital information.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

II. Example Embodiment

Figure 2:
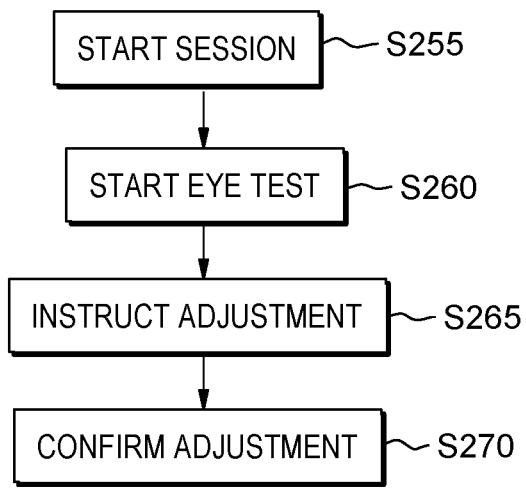
FIG. 2 is a flowchart showing a first embodiment method performed, at least in part, by the first embodiment system.
Figure 3:
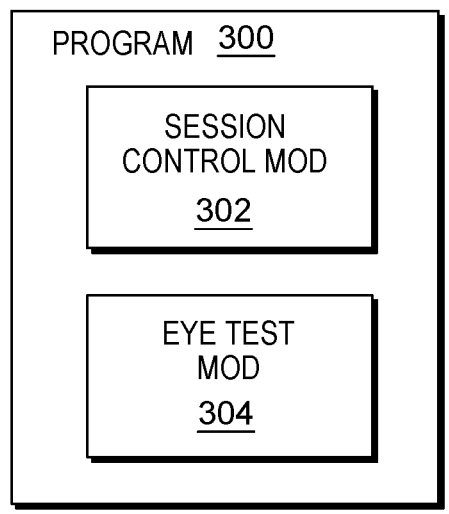
FIG. 3 is a block diagram showing a machine logic (for example, software) portion of the first embodiment system.

As shown in FIG. 1, networked computers system 100 is an environment in which an example method according to the present invention can be performed. As shown in FIG. 2, flowchart 250 shows an example method according to the present invention. As shown in FIG. 3, program 300 performs or controls performance of at least some of the method operations of flowchart 250. This method and associated software will now be discussed, over the course of the following paragraphs, with extensive reference to the blocks of FIGS. 1, 2 and 3.

Processing begins at operation S255, where session control module ("mod") 302 opens a data communication session between an end user computer system (that is, client subsystem 104) of a first user (not separately shown in the Figures) and remote eye test server computer (that is, server computer 200) over communication network 114.

Processing proceeds to operation S260, where, during the data communication session started at operation S255, eye test mod 304 administers an automated eye test that tests a set of characteristic(s) relating to vision of the first user.

Processing proceeds to operation S265, where, during the eye test started at operation S260, sending, by eye test mod 304 of eye test server computer an instruction to client subsystem 104 (and its user) to make an environmental adjustment. The environmental adjustment includes at least one of the following three types of environmental adjustment: an adjustment of a location of a first lamp included in an environment in which the first user computer system and the first user are located, an adjustment of a brightness level of the first lamp and/or an adjustment of a visual display setting of a first visual display included in an environment in which the first user computer system and the first user are located.

Processing proceeds to operation S270, where eye test mod 304 receives a first confirmation communication indicating that the environmental adjustment has been made. In this way, the eye test can continue under appropriate environmental conditions.

III. Further Comments and/or Embodiments

Some embodiments of the present invention recognize the following facts, potential problems and/or potential areas for improvement with respect to the current state of the art: (i) performing remote and active eye performance monitoring is difficult as it requires specialized and expensive medical devices, and medical expert guidance; (ii) the approaches do not consider environmental lighting in which the user is operating; (iii) there is little to no linkage or integration between a patients impairment (and its evolution) and their surroundings; and/or (iv) these barriers lead to a lack of sufficient eye testing to identify early changes in visual performance that may be indicative of deterioration and disease onset.

Some embodiments of the present invention may include one, or more, of the following operations, features, characteristics and/or advantages: (i) focuses on collecting a user's profile (visuo-mechanics base line of interaction in a lighting environment and a screen based device configuration) to run automated tests to study changes in eye performance informed by clinical guidelines; (ii) uses ambient configuration and screen based device configurations, resulting in changes being notified to the user; and/or (iii) new knowledge is added to the EMR (electronic medical record).

Some embodiments of the present invention may include one, or more, of the following operations, features, characteristics and/or advantages: (i) orchestrates the environment of the user (IoT (internet of things) devices that contribute to ambient lighting); (ii) orchestrates a device's visual settings to facilitate interaction under different "screen setting and ambient light testing conditions" to remotely and automatically study visuo-mechanics of the eye; (iii) learns about a user's visual profile over time towards detecting changes in performance, as early indicators, to recommend a visit to a clinician that receives the collected data to update the EMR; and/or (iv) orchestrates light contributing smart devices (for example, light bulbs, LED (light emitting diodes), light strips, intelligent curtains, electrochromic glass, and/or user worn auto shading glasses) in a setting (for example, home, work, hospital, truck, and/or pilot cockpit) to facilitate the lighting conditions during interaction to conduct automated data collection of visuo-mechanics of the eye to create a patient profile under different lighting conditions.

Some embodiments of the present invention may include one, or more, of the following operations, features, characteristics and/or advantages: (i) does not require predefined lenses, as each users' environment and lighting available setting are different; (ii) offers personalization based on: (a) the available sources, and/or (b) the user preferences while the user is moving in space for dynamic adjustment; (iii) does not require focusing on replicating natural light using a single lamp; and/or (iv) considers current eye disease to suggest lighting profiles that the user can adjust based on the orchestration of the IoT lighting resources in their environment.

Some embodiments of the present invention may include one, or more, of the following operations, features, characteristics and/or advantages: (i) focuses on collecting a user's profile (visuo-mechanics base line of interaction in a lighting and device configuration) to run automated tests to study changes in eye performance by using ambient configurations and screen based device configurations; (ii) uses home-based testing diagnostics; (iii) focuses on the eye and the visuo-mechanics of the eye; (iv) takes into account the visuo-mechanics of the eye and the change of device settings to create automated tests; and/or (v) uses the visuo-mechanics of the eye of an individual and adjusts the surroundings accordingly.

Some embodiments of the present invention may include one, or more, of the following operations, features, characteristics and/or advantages: (i) orchestrates the environment of the user (IoT devices that contribute to ambient lighting) and a device's visual settings to facilitate interaction under different "screen settings and ambient light testing conditions" to study visuo-mechanics of the eye; (ii) generates a user's visual profile (benchmark), for example, how do a user's eyes behave in a specific "screen setting and ambient light conditions"; (iii) automatically runs different "screen settings and ambient light conditions" to study changes in the performance obtained from medical guidelines (for example, when users have a condition that results in sensitivity to bright light, or where the users eyes take time to adapt to changes in lighting); (iv) the data collected is associated with EMR include remote monitoring in an outside environment; and/or (v) the fluctuation in performance can trigger alerts to visit a doctor, or recommendations for eye rest exercises.

Some embodiments of the present invention may include one, or more, of the following operations, features, characteristics and/or advantages: (i) draws from ophthalmological medical literature knowledge bases that list eye symptoms across different disease stages, for example, in stage two of age-related macular degeneration (AMD), it is suggested that a patient can become sensitive to white light; (ii) the knowledge from (i) above can be used to design automated eye tests "eye audit" settings (environment and device settings) and then coordinates technological arrangements; and/or (iii) uses the user's computing device (such as a smartphone, watch, or portable screen-based device with a built-in camera, position sensors such as gyroscope, and accelerometers) to track: (a) the user's visuo-mechanics of the eye, (b) the proximity of the device to the user's face, (c) the visual settings of the device (font, lighting, etc.), and/or (d) while interacting, position sensors derive the possible posture of the user's body, based on the angle of the device, and the proximity to the user's face.

Some embodiments of the present invention may include one, or more, of the following operations, features, characteristics and/or advantages: (i) monitors patients in a non-invasive manner to generate and complement medical insights; (ii) is relevant to existing artificial intelligence in medicine applications/services, IoT, and aged care; (iii) supports workers to work more efficiently through a dynamic lighting adjustment using all IoT devices, at home or at a work location; (iv) uses dynamic lighting preferences which are portable on the user's devices; (v) results in potentially increased productivity for the worker while their visuo-mechanics are collected; and/or (vi) the aggregated data of users, with known conditions, can offer a data set that feedbacks into a medical database on eye disease progression sensitivity to extend medical knowledge.

Some embodiments of the present invention will now be described using the following two (2) use cases:

Use Case 1: A patient suffers from light sensitivity due to their age related macular degeneration (AMD) condition, which is at stage 2 in both eyes. This stage is known for causing discomfort above certain lux levels as derived from medical literature. The user has enabled embodiments of the present invention in their home environment, linking their smart lightbulbs, smart curtains, and screen settings on all screen-based devices. The user then has the option to enter their eye test results or select from various test settings that alter the environment as they move within the space. This results in a lighting calibration that the user selects. This profile calibration is adjusted based on the time of day, the location within the space, the user's proximity to devices, and the device's settings to replicate the calibration profile and offer the user their preferred lighting settings.

Use Case 2: The ophthalmologist knows that this patient has enabled embodiments of the present invention and asks the patient for permission to run a few automated tests to study the patient's visuo-mechanics. The patient agrees, and the automated tests are, for example, in relation to lux level changes, contrast changes, brightness, light to dark eye adjustment, and eye saccade movements for mental acuity. This allows the clinician to run AI-driven automated tests that can complement clinical knowledge and indicate degeneration and progression so that interventions can be explored for the patient's eye.

Figure 4:
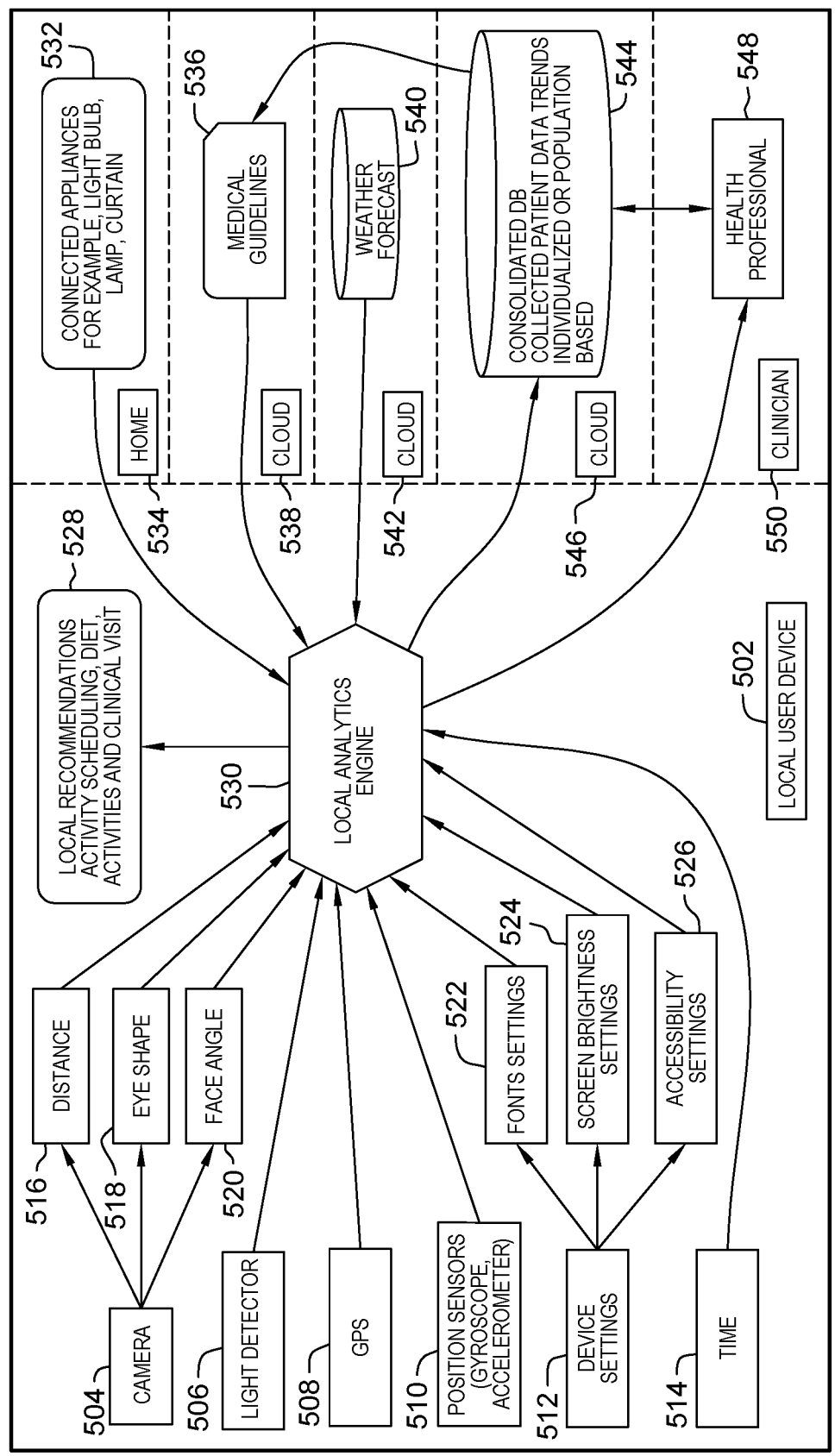
FIG. 4 is a block diagram of a second embodiment of a system according to the present invention.

As shown in FIG. 4, system 500 for administering remote eye tests includes: local user device block 502; camera block 504; light detector block 506; GPS (global positioning system) block 508; position sensors (gyroscope, accelerometer) block 510; device settings block 512; time block 514; distance block 516; eye shape block 518; face angle block 520; fonts settings block 522; screen brightness settings block 524; accessibility settings block 526; local recommendations activity scheduling, diet, activities and clinician visit block 528; local analytics engine block 530; connected appliances for example, light bulb, lamp, curtain block 532; home block 534; medical guidelines block 536; cloud block 538; weather forecast storage 540; cloud block 542; consolidated DB (database) collected patient data trends individualized or population based storage 544; cloud block 546; health professional block 548; and clinician block 550.

A method according to an embodiment of the present invention includes the following operations (not necessarily in the following order): (i) the patient installs on his/her mobile device an application that comprises a local analytics engine and a local historical database; (ii) using a unique patient identifier the application is linked to a remote consolidated database; (iii) during the setup phase, the device and the application can be paired with the user connected home network; (iv) as the patient uses the device, the application is stored in the local database where it uses a timestamped sensor, setting, position and time information; (v) the metrics described above are sampled at given tunable intervals or triggered by specific events including: (a) a camera is used to capture movement changes pertaining to the eye area, such as distance and the angle at which the patient interacts with the device, (b) a light detector is used to capture ambient light of the interaction, and (c) the device settings include screen brightness, font sizes and other accessibility features (for example, contrast, colors, etc.); and (vi) triggering events include (but are not limited to): (a) a change in the device settings, (b) a change in the physical location as indicated by GPS (global positioning system) coordinates, (c) a change in the light conditions, and (d) an application initiated test.

A method according to an embodiment of the present invention includes the following operations (not necessarily in the following order): (i) the set of data described in the paragraph above is locally logged for an initial duration to calibrate the application and to learn a baseline model of the user where; (a) this baseline can be altered by the patient specific data, (b) manually inputted during the application setup, (c) data is locally aggregated so that trends, as opposed to absolute data, is considered, and (d) the local systems continuously learn and adjust based on the triggers and data captured; and (ii) after the calibration period, the local analytics engine will produce inferences and start emitting recommendations and become active, for example: (a) based on patient specific data and screen brightness settings, it will adjust the home lightning, system or curtains, (b) based on screen brightness and usual ambient light, it will advise the best time of the day for specific activities where, in this case, other inputs will include weather data and traffic data, and (c) based on observed trends in the device usage and medical guidelines it will create an alert for medical consultation for "just in time" examination and treatment, where needed, including visual performance metrics that deviate from the user's profile benchmark.

A method according to an embodiment of the present invention includes the following operations (not necessarily in the following order): (i) trends logged by the local analytics engine are periodically uploaded to the consolidated DB (database) and made available to the medical specialist following the patient; (ii) the anonymized data will also be stored and feed into the overall medical guidelines and serve as observation points; (iii) the medical specialist can alter the application recommendations through this database (he/she has no direct access to the patient device) where: (a) the medical specialist can request the application to run periodic patient visual tests, and (b) the medical specialist can override the recommendations/actions taken by the analytics engine where such an override serves as input to the learning process of the device engine; and (iv) the local device DB is backed up in the cloud and can be restored as needed to preserve historical data.

Some embodiments of the present invention may include one, or more, of the following operations, features, characteristics and/or advantages: (i) automatically and remotely use day to day devices to learn about visuo-mechanics of the eye; (ii) the system flags changes in eye performance from a benchmark and this may be used to alert the user to visit a doctor, or take a rest from screen based devices; (iii) suggests digital device settings that can support the user as a result of analyzing device usage, proximity, blinking rate, squinting to read, eye dryness, and screen light current settings; (iv) generates a data log of interaction with the device and eye metric changes that can serve the individual, as well as aggregated for clinicians and researchers to further study early manifestations of disease onset; (v) drivers, pilots, athletes, and medical surgeons can also be audited to review mental acuity from changes in eye performance; and/or (vi) update EMR from a remote monitor so that the clinician and medical models have access to more time series data to study the patient.

Some embodiments of the present invention may include one, or more, of the following operations, features, characteristics and/or advantages: (i) produces inferences and emitting recommendations by the local analytics engine after the calibration period, wherein the recommendations can adjust the home lightning system or curtains based on patient specific data and screen brightness settings; (ii) advises the best time of day for specific activities based on screen brightness and usual ambient light; (iii) creates an alert for medical consultation for just in time examination and treatment, where needed, where visual performance metrics deviate from the user's profile benchmark based on observed trends in the device usage and medical guidelines; and/or (iv) uploads logged trends on the local analytics engine to the consolidated database.

Some embodiments of the present invention may include one, or more, of the following operations, features, characteristics and/or advantages: (i) provides uploaded trends of the user to the medical specialist; (ii) stores the anonymized data and feeds it into the overall medical guidelines to serve as observations points; (iii) alters the recommendations through the consolidated database (the user has no direct access to the device) by the application or by the medical specialist, wherein the alteration in the recommendation may run periodic patient visual tests based on the request of the medical specialist; (iv) overrides the recommendations/ actions taken by the analytics engine where such an override serves as input to the learning process of the device engine by the medical specialist; and/or (v) when needed, restores the local device database, which is backed up in the cloud, to preserve historical data.

IV. Definitions

Present invention: should not be taken as an absolute indication that the subject matter described by the term "present invention" is covered by either the claims as they are filed, or by the claims that may eventually issue after patent prosecution; while the term "present invention" is used to help the reader to get a general feel for which disclosures herein are believed to potentially be new, this understanding, as indicated by use of the term "present invention," is tentative and provisional and subject to change over the course of patent prosecution as relevant information is developed and as the claims are potentially amended.

Embodiment: see definition of "present invention" above—similar cautions apply to the term "embodiment."

and/or: inclusive or; for example, A, B "and/or" C means that at least one of A or B or C is true and applicable.

Including/include/includes: unless otherwise explicitly noted, means "including but not necessarily limited to."

Module/Sub-Module: any set of hardware, firmware and/ or software that operatively works to do some kind of function, without regard to whether the module is: (i) in a single local proximity; (ii) distributed over a wide area; (iii) in a single proximity within a larger piece of software code; (iv) located within a single piece of software code; (v) located in a single storage device, memory or medium; (vi) mechanically connected; (vii) electrically connected; and/or (viii) connected in data communication.

Computer: any device with significant data processing and/or machine readable instruction reading capabilities including, but not limited to: desktop computers, mainframe computers, laptop computers, field-programmable gate array (FPGA) based devices, smart phones, personal digital assistants (PDAs), body-mounted or inserted computers, embedded device style computers, application-specific integrated circuit (ASIC) based devices.

What is claimed is:

1. A computer implemented method (CIM) comprising:
opening a data communication session between an end user computer system of a first user and a remote eye test server computer over a communication network, wherein the end user computer system is located in an environment of the first user and is paired with Internet of Things (IoT) devices that contribute to ambient light in the environment;
during the data communication session, administering, by the eye test server computer, an automated eye test that tests a set of characteristic(s) relating to vision of the first user;
during the administration of the automated eye test, sending, by the eye test server computer, over the communication network and to the end user computer system, an instruction that causes a local analytics engine on the end user computer system to make an adjustment to screen settings of the end user computer system and an adjustment to one or more of the IoT devices to facilitate interactions under different screen settings and ambient light testing conditions;
collecting data via one or more sensors in the end user computer system during the administration of the automated eye test under the different screen settings and ambient light testing conditions, the data including: tracking visuo-mechanics of an eye of the first user; proximity of the end user computer system to a face of the first user; and visual settings of the end user computer system;
generating a visual profile of the first user including user specific data of the first user based on the administration of the automated the eye test under the different screen settings and ambient light testing conditions; and
automatically adjusting a respective one of the IoT devices in the environment of the first user based on the user specific data and current screen brightness settings of the end user computer system,
wherein the respective one of the IoT devices comprises a smart lighting system or a smart curtain in the environment of the first user.

2. The CIM of claim 1 further comprising:
producing a plurality of inferences, by the local analytics engine, after a calibration period.

3. The CIM of claim 1 further comprising:
producing at least one recommendation, by the local analytics engine, after a calibration period.

4. The CIM of claim 1 further comprising:
advising an optimal time of day for specific eye test related activities based on at least one of the following: screen brightness and usual ambient light.

5. The CIM of claim 1 further comprising:
creating an alert for medical consultation for just in time examination and treatment based on visual performance metrics of the first user deviating from a baseline in the visual profile of the first user and medical guidelines; and
uploading logged trends on a local analytics engine to a consolidated database.

6. A computer implemented method (CIM) comprising:
opening a data communication session between an end user computer system of a first user and a remote eye test server computer over a communication network;
during the data communication session, administering, by the eye test server computer, an automated eye test that tests a set of characteristic(s) relating to vision of the first user;
during the administration of the automated eye test, sending, by the eye test server computer, over the communication network and to the end user computer system, an instruction that causes a local analytics engine on the end user computer system to make an adjustment to screen settings of the end user computer system and an adjustment to one or more of the IoT devices to facilitate interactions under different screen settings and ambient light testing conditions;
learning a baseline of the first user based on the eye test;
altering the baseline based on user specific data; and
automatically adjusting a respective one of the IoT devices comprising a smart lighting system in the environment of the first user based on the user specific data and screen brightness settings of the first user computer system in the environment of the first user.

7. A computer implemented method (CIM) comprising:
opening a data communication session between an end user computer system of a first user and a remote eye test server computer over a communication network;
during the data communication session, administering, by the eye test server computer, an automated eye test that tests a set of characteristic(s) relating to vision of the first user;
during the administration of the automated eye test, sending, by the eye test server computer, over the communication network and to the end user computer system, an instruction that causes a local analytics engine on the end user computer system to make an adjustment to screen settings of the end user computer system and an adjustment to one or more of the IoT devices to facilitate interactions under different screen settings and ambient light testing conditions;
learning a baseline of the first user based on the eye test;
altering the baseline based on user specific data; and
automatically adjusting a respective one of the IoT devices comprising a smart curtain in the environment of the first user based on the user specific data and screen brightness settings of the first user computer system in the environment of the first user.

8. The CIM of claim 1, wherein the automatically adjusting the respective one of the IoT devices in the environment of the first user is performed by the local analytics engine.

9. The CIM of claim 8, further comprising the local analytics engine automatically advising the first user of an optimal time of day for a specific activity based on screen brightness and usual ambient light.

10. The CIM of claim 8, wherein the automatically adjusting the respective one of the IoT devices in the environment of the first user comprises dynamically adjusting the respective one of the IoT devices while the first user is moving within a space to provide the first user with preferred lighting settings.

\* \* \* \* \*